United States Patent [19]

Harnisch et al.

[11] Patent Number: 4,659,657
[45] Date of Patent: Apr. 21, 1987

[54] CHROMOGENIC AND FLUOROGENIC ESTERS FOR PHOTOMETRIC OR FLUORIMETRIC DETERMINATION OF PHOSPHATASES OR SULPHATASES

[75] Inventors: Horst Harnisch, Much, Fed. Rep. of Germany; Otto S. Wolfbeis, Graz, Austria

[73] Assignee: Bayer Aktiengesellschaft, Leverkusen, Fed. Rep. of Germany

[21] Appl. No.: 561,391

[22] Filed: Dec. 14, 1983

[30] Foreign Application Priority Data

Dec. 24, 1982 [DE] Fed. Rep. of Germany ....... 3248043
Jun. 10, 1983 [DE] Fed. Rep. of Germany ....... 3321041

[51] Int. Cl.$^4$ .......................... C12Q 1/42; C12Q 1/34; C07D 405/04
[52] U.S. Cl. ........................................ 435/21; 435/18; 544/244; 544/287; 546/22; 546/23; 546/155; 546/156; 546/157; 546/269; 548/112; 548/113; 548/119; 548/136; 548/143; 548/159; 548/204; 548/217; 548/327; 549/220; 549/285; 549/286; 549/287; 549/288; 549/289
[58] Field of Search ................ 544/287, 244; 424/257; 546/22, 23, 155-157, 269; 548/112, 113, 119, 136, 143, 159; 514/81-82, 89, 92, 100, 94, 259, 311-314, 337, 367, 363-365; 435/18, 21

[56] References Cited

U.S. PATENT DOCUMENTS 4,585,598 4/1986 Harnisch .............................. 435/21

OTHER PUBLICATIONS

Cooper, et al., "Chemical Abstracts", vol. 62, 1965, col. 9112f.
Cooper, et al., "Chemical Abstracts", vol. 57, 1962, col. 13729f.
Cooper, et al., "Chemical Abstracts", vol. 64, 1966, col. 2061d.
The Enzymes, vol. 5, 1961, pp. 38-44, 58-71, p. 45, second edition-completely revised by Paul D. Boyer et al.

Primary Examiner—Glennon H. Hollrah
Assistant Examiner—James H. Turnipseed
Attorney, Agent, or Firm—Sprung Horn Kramer & Woods

[57] ABSTRACT

Compounds of the formula

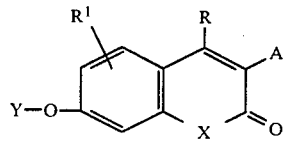

wherein
Y is

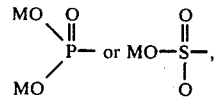

M is hydrogen, or an alkali metal or ammonium ion,
X is —O— or an amino group,
R is H, Cl, Br, CN or carbamoyl,
R$^1$ is H or —SO$_3$H, and
A is one of several particular organic radicals, are especially useful in the photometric or fluorimetric determination of phosphatase or sulphatase activity in a liquid sample.

12 Claims, No Drawings

CHROMOGENIC AND FLUOROGENIC ESTERS FOR PHOTOMETRIC OR FLUORIMETRIC DETERMINATION OF PHOSPHATASES OR SULPHATASES

The present invention relates to new chromogenic and fluorogenic phosphoric acid esters and sulphuric acid esters which form a highly fluorescent colored anion under the influence of phosphatases or, respectively, sulphatases and can be used for an improved photometric or fluorimetric determination method for phosphatases and sulphatases.

Photometric methods for the determination of phosphatases have been known for a relatively long time. In clinical analysis, N-nitrophenyl phosphate, which is split into p-nitrophenol and phosphate by a phosphatase, is almost exclusively used. The increase in extinction of the phenolate is measured as a function of time. The formation of the phenolate is achieved by adding alkali, but the enzymatic reaction is thereby also interrupted. This is therefore an end point method (Bergmeyer, Methoden der enzymatischen Analyse (Methods of enzymatic analysis), Volume 1, page 888, Verlag Chemie, Weinheim, 1974).

Fluorimetric methods for the determination of phosphatase activities have also been known for a relatively long time (Guilbault, Enzymatic Methods of Analysis, Pergamon Press (1970). Fluorimetry is so sensitive that even extremely low enzyme concentrations can be detected and determined by this method. Known phosphatase reagents used in fluorimetry are phosphoric acid esters of umbelliferone (G. G. Guilbault et al., Anal. Letters 1, (1968) (333), of 4-methylumbelliferone (H. N. Fernley, P. G. Walker, Biochem. J. 97 (1965) (95), of flavonol (D. B. Land, E. Jakim, Anal. Biochem. 16 (1966) (481), of α-naphthol (D. W. Moss, Clin. chim. Acta 5 (1960) (283), of β-naphthol (L. J. Greenberg, Biochem. Biophys. Res. Comm. 9 (1962) (430) and of 3-O-methyl-fluorescein (H. D. Hill et al., Anal. Biochem. 24 (1968) (9).

These known detection methods are not completely satisfactory for various reasons. In the case of various absorbents of fluorescent enzyme substrates, troublesome overlapping of the absorption or fluorescence with that of the material under investigation occurs. In the case of enzyme substrates with a small shift between the absorption bands of the substrate and of the chromophor or fluorophor liberated, too marked an overlapping of the two bands occurs, which reduces the accuracy of the method. Moreover, at present, there is still no method known which permits direct kinetic monitoring of enzymatic splitting reactions by phosphatases in the visible range of absorption or fluorescence excitation.

Furthermore, sufficiently rapid splitting of phosphoric acid esters of the abovementioned prior art for them to be used in clinical analysis takes place only in the alkaline pH range. However, for diagnosis, for example for the early recognition of carcinomas of the prostate, it would also be important to determine acid phosphatase activities.

U.S. Pat. No. 3,772,340 describes bis-coumarinyl phosphates which are intended to be used for fluorimetric determinations of phosphodiesterases such as occur in urine containing bacteria. A disadvantage of these compounds is that they are sparingly soluble in water, which limits their practical application.

Photometric methods for the determination of sulphatases have also been known for a relatively long time. Thus, Roy (Biochem. Journal 62 (1956) (41) uses nitrocatechol sulphate, which is split into sulphate and nitrocatechol by a sulphatase, as the substrate. The formation of the nitrocatechol is monitored photometrically. Leon et al. (Biochem. J. 75 (1960) (612) use p-nitrophenyl sulphate in the same sense. Dodgson and Spencer (Biochem. J. 55 (1953) (315) use p-acetylphenyl sulphate.

Fluorimetric methods for the determination of sulphatase activities likewise belong to the prior art (Guilbault, Enzymatic Methods of Analysis, Pergamon Press 1970). The fluorimetry is so sensitive that even extremely low enzyme concentrations can be detected and determined using this method. Known sulphatase reagents used in fluorimetry are sulphuric acid esters of various fluorophors. Sherman and Stanfield (Biochem. J. 102 (1967) (905) use 4-methylumbelliferone sulphate for the determination of aryl-sulphatase with the aid of an end point method, and Guilbault and Hiersermann have investigated a number of sulphuric acid esters (for example of indoxyl, β-naphthol, 4-methylumbelliferone, fluorescein and resorufin) in respect of their suitability for direct kinetic determination of sulphatases (Anal. Chem. 41 (1969), (2006).

However, these known detection methods for sulphatases are likewise not completely satisfactory for various reasons: the sulphuric acid esters of the prior art mentioned are split rapidly enough only at relatively high enzyme concentrations and can therefore hardly be used in clinical analysis. However, for diagnosis, for example in the early recognition of certain hereditary diseases, it would be important to determine even the smallest activities. Moreover, troublesome overlapping of the fluorescence of the ester and of the anion formed during hydrolysis occurs with many of the known fluorogenic sulphuric acid esters. In addition, some of the reagents of the prior art also require substantial expenditure on apparatus.

The object of the present invention is to provide reagents for the photometric and fluorimetric detection of phosphatases or sulphatases which are free from the abovementioned disadvantages of the prior art. This object is achieved by means of the phosphoric acid esters and sulphuric acid esters according to the invention.

The invention relates to new esters of the general formula

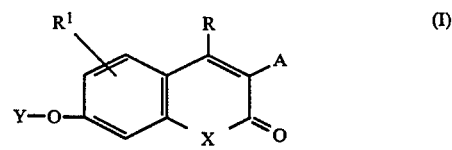

(I)

wherein
Y denotes an acid radical

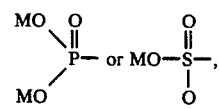

M represents hydrogen or an alkali metal, pyridinium or ammonium ion, which can be substituted by 1-4

$C_1$–$C_2$-alkyl radicals optionally containing a hydroxyl group,

X represents —O— or —NQ—,

Q represents hydrogen, $C_1$–$C_4$-alkyl which is optionally substituted by 1–2 OH groups, or $C_1$–$C_4$-alkoxycarbonyl, R represents hydrogen, chlorine, bromine, cyano or carbamoyl, A represents cyano, $C_1$–$C_4$-alkoxycarbonyl, or carbamoyl or sulphamoyl which is optionally substituted by 1–2 $C_1$–$C_4$-alkyl radicals, or $C_1$–$C_4$-alkylsulphonyl, benzylsulphonyl, phenylsulphonyl, p-tolylsulphonyl, p-chlorophenylsulphonyl, sulpho, nitro, phenyl, p-tolyl, sulphophenyl, or a benzoxazol-2-yl, benzothiazol-2-yl, thiazol-2-yl, benzimidazol-2-yl, quinazol-4-on-2-yl, 5-phenyl-1,3,4-thiadiazol-2-yl, 5-phenyl-1,3,4-oxadiazol-2-yl, or 2- or 4-pyridyl radical which is optionally substituted by 1–2 $C_1$–$C_4$-alkyl radicals, 1–2 chlorine atoms, $C_1$–$C_4$-alkoxy, carboxyl, $C_1$–$C_4$-alkoxycarbonyl, cyano, trifluoromethyl, $C_1$–$C_4$-alkylsulphonyl, cyclohexyl, phenyl or sulpho, and $R^1$ represents hydrogen or a sulphonic acid group.

Preferred compounds of the general formula (I) are those in which

A represents a benzoxazol-2-yl, benzothiazol-2-yl, thiazol-5-yl, benzimidazol-2-yl, quinazol-4-on-2-yl, 5-phenyl-1,3,4-thiadiazol-2-yl or 4-pyridyl radical which is optionally substituted by 1–2 $C_1$–$C_4$-alkyl radicals, 1–2 chlorine atoms, $C_1$–$C_4$-alkoxy, $C_1$–$C_4$-alkylsulphonyl, carboxyl, $C_1$–$C_4$-alkoxycarbonyl, cyclohexyl, phenyl or sulpho.

Particularly preferred compounds of the formula (I) are those wherein

A represents a benzothiazol-2-yl or benzoxazol-2-yl radical which is optionally substituted by methyl, ethyl, chlorine, methoxy, ethoxy or sulpho and R represents CN.

The phosphoric acid esters of the formula (I) according to the invention can be prepared by a process in which hydroxy compounds of the formula

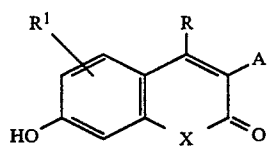

(II)

wherein

X, A, R and $R^1$ have the abovementioned meaning, are first reacted with a halide of 5-valent phosphorus (optionally in the presence of an inorganic or organic acid-trapping agent), and the resulting dihalogenophosphonyloxy compound is then hydrolyzed.

Examples of halides of 5-valent phosphorus are phosphorus oxytrichloride, phosphorus oxytribromide and phosphorus pentachloride, the latter preferably being used if the molecule contains a sulpho group (temporary conversion into the corresponding sulphochloride).

Suitable acid-trapping agents are inorganic or organic bases, for example anhydrous potassium or sodium carbonate, magnesium oxide, triethylamine, collidine, picoline mixtures, pyridine and dimethylaniline.

The reaction is preferably carried out in the presence of a solvent or a diluent in the temperature range from −5° to 100° C., preferably at 0°–30° C. in the case of the phosphorus oxytrihalides and preferably at 20°–90° C. in the case of $PCl_5$.

Suitable solvents or diluents are organic liquids which are inert under the reaction conditions, such as toluene, chlorobenzene, dichlorobenzene, methylene chloride, chloroform, carbon tetrachloride, dichloroethane, dichloropropane, trichloroethylene, acetonitrile, dioxane, tetrahydrofuran or one of the abovementioned organic bases, such as pyridine.

In order to avoid reaction of the 5-valent phosporus halide with 2 molecules of (II), an excess of phosphorus halide is advantageously ensured during the reaction by adding (II) gradually as the last component, if appropriate predissolved in one of the abovementioned solvents.

The hydrolysis of the intermediate dichlorophosphonyloxy compounds to give (I) can be carried out, for example, by careful warming with water to about 50° C., but under milder conditions at temperatures of 0°–25° C. by neutralization with alkali metal hydroxide solution or alkali metal carbonate solution, pyridine or aqueous ammonia. The resulting alkali metal salts or ammonium salts are then evaporated to dryness in vacuo, or the free acid (I in which M=H) is isolated by acidification with a mineral acid, such as sulphuric acid, and filtration.

The sulphuric acid esters of the formula (I) according to the invention can be prepared by a process in which hydroxy compounds of the formula (II)

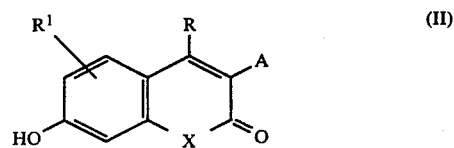

(II)

are reacted with chlorosulphonic acid in an organic solvent (preferably in the presence of an inorganic or organic base-trapping agent) and the resulting sulphuric acid monoester is isolated in the form of a salt. The reaction can also be carried out with sulphuryl chloride ($SO_2Cl_2$) in a corresponding manner, in which case a sulphuric acid monoester chloride is intermediately formed, and is converted into the free sulphonic acid or into one of its salts by subsequent hydrolysis.

Suitable acid-trapping agents are all the abovementioned inorganic and organic bases.

The reaction is preferably carried out in the presence of a solvent or diluent in the temperature range from −5° to 100° C., preferably at 0°–30° C. in the case of sulphuryl chloride.

Suitable solvents and diluents are all the organic liquids which have already been described above and are inert under the reaction conditions, or one of the abovementioned organic bases, such as pyridine.

In order to avoid reaction of the sulphuric acid dihalide with 2 molecules of (II), an excess of acid halide is advantageously ensured during the reaction by adding (II) gradually as the last component, if appropriate predissolved in one of the abovementioned solvents.

The hydrolysis of the intermediate sulphuric acid monoester chlorides to give (I) can likewise be carried out, for example, by careful warming with water to about 50° C., but under milder conditions at temperatures of 0°–25° C. by neutralization with alkali metal hydroxide solution or alkali metal carbonate solution, pyridine or aqueous ammonia. The resulting alkali metal salts or ammonium salts are then evaporated to dryness in vacuo, or the free acid (I in which M=H) is obtained by acidification with a mineral acid, such as sulphuric acid, and by filtration.

The methods described above for O-phosphorylation or O-sulphonylation of (II) essentially agree with the general methods described in Houben-Weyl, Methoden der Organischen Chemie (Methods of organic chemistry), Volume XII/2 (1964), pages 172–177, or Volume IX (1955), page 665, for the phosphorylation or O-sulphonylation of aromatic hydroxy compounds.

The starting compounds of the formula (II) are known (U.S. Pat. No. 3,521,187, Compound 11; DE-OS (German Published Specification) No. 2,702,337; DE-OS (German Published Specification) No. 3,044,128, DE-OS (German Published Specification) No. 2,100,295 and DE-OS (German Published Specification) No. 3,229,301) or they can be prepared by the methods mentioned therein.

The new compounds of the formula (I) are water-soluble and have a pale blue (R=H, Cl or Br) or greenish (R=CN or $CONH_2$) fluorescence, and in most cases are only slightly colored substances, which are split by alkaline or acid phosphatase or sulphatase in an aqueous medium to give the highly fluorescent, deep yellow-to-red colored mesomeric anion of the formulae

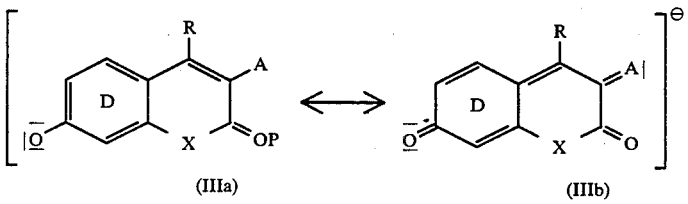

(IIIa)    (IIIb)

The new phosphatase or sulphatase reagents of the formula (I) are therefore suitable for direct phosphatase or sulphatase detection in biological materials. They can be particularly advantageously used for the quantitative photometric and fluorimetric determination of alkaline or acid phosphatases or sulphatases in clinical analysis.

Compared with the phosphatase reagents of the prior art, the new phosphoric acid esters of the formula (I) have substantial advantages:

1. No overlapping at all of the absorption band of the phenolate ion formed on enzymatic hydrolysis (IIIa–IIIb) in relation to the absorption of the phosphoric acid esters because of the high Stokes shift, so that the increase in absorption of the phenolate ion can easily be monitored photometrically.

2. No troublesome overlapping at all of the powerful fluorescence, which is obtained on enzymatic splitting of (I) and is to be monitored fluorimetrically, of the phenolate (IIIa–IIIb) with the weak fluorescence of the reagent (I) employed (high Stoke's shift).

3. The use of an extremely simple filter fluorimeter is possible, since neither excitation by UV light, in the case of which the background fluorescence of the biological material as a rule noticeably interferes, nor the use of expensive monochromators or interference filters, such as are used when 3-O-methylfluorescein phosphate is employed, are required.

4. Formation of the deep-colored fluorescent phenolate ion (IIIa–IIIb) surprisingly already occurs under weakly acid conditions (for example at pH 5.2). It is thus possible, for the first time, to monitor the activity of acid phosphatases photometrically or fluorimetrically in the visible range of the spectrum in a continuous measurement with a detection sensitivity as high as that which has hitherto been known only with the more time-consuming non-kinetic methods.

The phosphoric acid esters according to the invention can be used for the determination of the phosphatase activity in the most diverse body fluids (serum; cerebrospinal fluid; urine). However, it is also possible to use the reagents according to the invention analogously to the teaching of U.S. Pat. No. 3,772,340, for the measurement of the concentration of bacteria in fluids (for example bacterially infected urine). For this purpose, the bacterial enzymes, including phosphatases, are first liberated in a manner which is known per se (for example osmotic shock; sphaeroplast formation). Conclusions as to the number of bacteria present can be drawn from the phosphatase activity determined by means of the compounds according to the invention.

The new sulphuric acid esters of the formula (I) also have substantial advantages in comparison with the sulphatase reagents of the prior art:

1. Because of the high molar light absorption of the mesomeric anions liberated (IIIa–IIIb), photometric monitoring of the enzymatic reaction in the long-wavelength range of the spectrum is for the first time possible.

2. No troublesome overlapping at all of the fluorescence of the phenolate (IIIa–IIIb) with the weak fluorescence of the reagent (I) used (see above).

3. It is possible to use an extremely simple filter fluorimeter, since neither excitation by UV light, in the case of which the background fluorescence of the biological material as a rule interferes noticeably, nor the use of expensive monochromators or interference filters, such as are used when fluorescein O-sulphate is employed, are required.

4. The deep-colored fluorescent hydroxylate anion (IIIa–IIIb) is surprisingly already formed under weakly acid conditions (for example at pH 5.2). It is thus for the first time possible to monitor the activity of sulphatases fluorimetrically in this range of the spectrum by continuous measurement with a detection sensitivity as high as that which has hitherto been known only for the more time-consuming non-kinetic methods.

The sulphuric acid esters according to the invention can also be used for the determination of the sulphatase activity in the most diverse body fluids (serum; cerebrospinal fluid; urine).

Because of their good water-solubility, the compounds according to the invention can be used in the form of aqueous solutions, if appropriate buffered at the desired pH value (for example about 4.5–7 for acid phosphatases; about 7–10 for alkaline phosphatases), for the determination of the phosphatase or sulphatase activity. However, it is also possible to apply the new esters to carriers in a manner which is in itself known and to allow the detection reaction to proceed in a heterogeneous phase system. Examples of suitable carrier materials are filter paper, or silicon dioxide which is applied to a plastic (for example polystyrene) and provided with an organic binder. In this way, it is possible to produce test strips which change color or start to fluoresce after application of the fluid to be investigated and of which the color or fluorescence can be measured by means of the photometers or fluorimeters customary in clinical analysis. Quantitative determination of the phosphatase or sulphatase activity in an unknown sample is possible if the course of the absorption light or of fluorescence intensity in the aqueous solution or on the test strip with respect to time is compared with that of standards of known phosphatase or sulphatase content.

The following phosphatase products from Messrs. Sigma Chemical Co. were used as standards in the phosphatase determination experiments described below:

(a) alkaline phosphatase (EC. 3.1.3.1):
Type I-S (P7640)
(from bovine testicle mucosa)

(b) acid phosphatases (EC 3.1.3.2):
Type III (P6760),
Type IV-S (P1146) and
Type V (P1267)
(from wheat germs, potatoes, milk and bovine testicles).

The following sulphatase products from Messrs. Sigma Chemical Co. were used as standards in the experiments for the determination of sulphatase:

(a) aryl-sulphatase (E.C. 3.1.6.1): Type V (S 8629), from *Patella vulgata*

(b) aryl-sulphatase (E.C. 3.1.6.1): Type VI (S 1629), from *Aerobacter aerogenes*

(c) aryl-sulphatase (E.C. 3.1.6.1): Type H-I (S 9626), from *Helix pomatia.*

EC is in each case the term for the internationally valid Enzyme Catalogue.

EXAMPLE 1

39 g (23 ml; 0.25 mol) of phosphorus oxytrichloride are added dropwise to 800 ml of dry pyridine at 0°–5° C., while cooling and stirring, 80 g (0.25 mol) of 3-benzothiazolyl-4-cyano-7-hydroxycoumarin are then added in portions at the same temperature in the course of about 30 minutes and the mixture is stirred at 0°–5° C. for 3 hours. It is poured onto 2 liters of ice-water, 66 g (45 ml; 0.75 mol) of 45% strength by weight sodium hydroxide solution are added dropwise, while stirring, a pH value of about 7 being established, the mixture is stirred for 10 hours and evaporated to dryness in vacuo with the aid of a rotary evaporator at 40° C. and the residue is further dried to constant weight of 40° C. in vacuo. The residue (185 g) consists of 44 g of sodium chloride and 141 g (96% of theory) of the compound of the formula For purification, the residue is recrystallized from ethanol/water (4:1). Orange-colored crystals of melting point 325° C. (decomposition) are obtained.

The compound is soluble, for example, in water, methanol, dimethylformamide, dimethylsulphoxide and ethylene glycol monomethyl ether.

For photometric monitoring of the enzymatic hydrolysis, the extinction of 510 nm is measured.

For fluorimetric monitoring of the enzymatic hydrolysis, excitation light with a maximum at 510 nm is chosen and the fluorescence is measured at 595 nm. At this wavelength, exclusively the fluorescence of the enzymatically split substrate is recorded.

The following phosphoric acid esters of the general formula are prepared analogously, using the corresponding starting compounds:

EXAMPLE 25

61,8 g of phosphorus pentachloride (0,3 mols) and then 22,6 g (0.05 mols) of 3-(5-methyl-7-sulpho-benzoxazol-2-yl)-7-hydroxycoumarin pyridinium salt are added to 225 ml of dry acetonitrile at 20°–30° C. while cooling and stirring, and the mixture is stirred for 18 hours at 20°–25° C. The mixture is poured onto 1.5 l of ice-water, 166 g (112 ml; 1.9 mols) of 45% strength by weight sodium hydroxide solution is added dropwise while stirring, a pH value of approx. 7 being established, and the mixture is stirred for 10 hours. The filtrate is evaporated to dryness within the aid of a rotary evaporator, and the residue is extracted with 2 l of boiling methanol. The extract is filtered at room temperature and evaporated to dryness; yielding 24,8 g of the compound of the formula For photometric monitoring of the enzymatic hydrolysis, the extinction at 430 nm is measured.

For monitoring the enzymatic hydrolysis by phosphatases, excitation is effected at about 450 nm in the fluorimeter and the emission is measured at about 495 nm. Virtually only the fluorescence of the enzymatically split substrate is recorded here.

The following phosphoric acid esters, containing sulpho groups, of the general formula are prepared analogously using the corresponding starting compounds:
| Example | M | R | A | X | Melting point (Decomposition) °C. |
|---|---|---|---|---|---|
| 2 | Na | H | 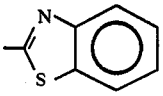 | O | 301° |
| 3 | K | CN | 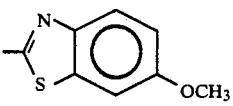 | O | 309° |
| 4 | Na | H | 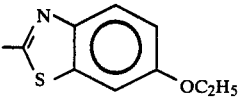 | O | 302° |
| 5 | Na | CN | 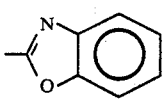 | O | 310° |
| 6 | NH$_4$ | H | 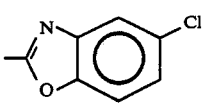 | O | 318° |
| 7 | K | CN | 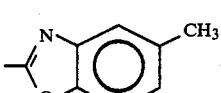 | O | 304° |
| 8 | Na | CN | 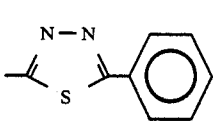 | O | 308° |
| 9 | Li | H | 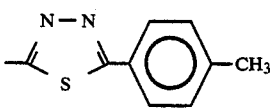 | O | 300° |
| 10 | Na | CN | 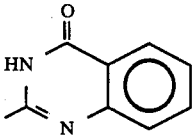 | O | 330° |
| 11 | K | CN | 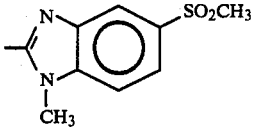 | O | 317° |
| 12 | Na | CN | 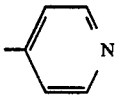 | O | 315° |
| 13 | NH$_4$ | H | 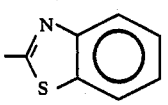 | N—C$_4$H$_9$—n | 300° |

-continued

| Example | M | R | A | X | Melting point (Decomposition) °C. |
|---|---|---|---|---|---|
| 14 | K | H | 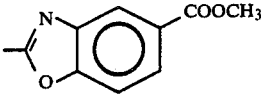 2-methylbenzoxazole-5-COOCH3 | N—CH3 | 313° |
| 15 | Na | H | 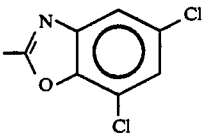 5,7-dichloro-2-methylbenzoxazole | N—COOC2H5 | 322° |
| 16 | H2N(C2H4OH)2 | CN | 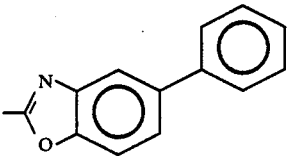 2-methyl-5-phenylbenzoxazole | O | 262° |
| 17 | HN(C2H5)3 | H | 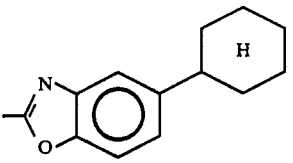 2-methyl-5-cyclohexylbenzoxazole | O | 278° |
| 18 | Na | CN | 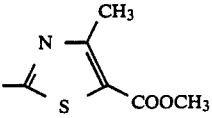 | O | 307° |
| 19 | K | CN | 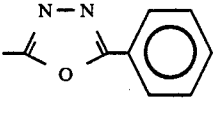 | O | 316° |
| 20 | Na | CN | CN | O | 327° |
| 21 | K | CN | COOCH3 | O | 304° |
| 22 | Na | CN | SO2CH3 | O | 312° |
| 23 | Na | CN | SO2—C6H5 | O | 326° |
| 24 | K | CN | 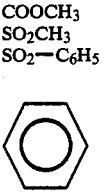 | O | 305° |
| 26 | Na | CN |  2-methylbenzothiazole | | |
| 27 | K | H |  2-methyl-6-methoxybenzothiazole | | |
| 28 | Na | CN |  2-methylbenzoxazole | | |
| 29 | Na | H | 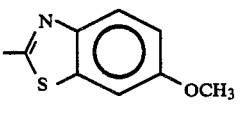 5-chloro-2-methylbenzoxazole | | |

-continued

| Example | M | R | A | X | Melting point (Decomposition) °C. |
|---------|---|---|---|---|---|
| 30 | Na | CN | ![structure with N, S, Cl, Cl] | | |

EXAMPLE 31

1.46 g (0.83 ml; 12.5 mmol) of chlorosulphonic acid are added dropwise to 5 ml of dry pyridine, while cooling and stirring, and the pyridine-chlorosulphonic acid complex formed is then dissolved by warming. After addition of 0.7 g (2.5 mmol) of 3-benzoxazolyl-7-hydroxycoumarin, the mixture is warmed at 60° C. for about 24 hours. 20 ml of water are added and the undissolved material is filtered off at the boiling point. On cooling, 0.8 g (73.5% of theory) of the compound of the formula

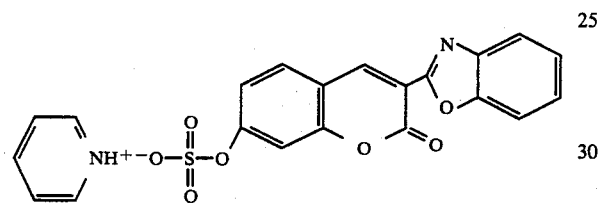

recrystallizes. The ochre-colored crystals have a melting point of 201°–202° C.

The compound is soluble, for example, in water, methanol, dimethylformamide, dimethylsulphoxide and ethylene glycol monomethyl ether.

For photometric monitoring of the enzymatic hydrolysis, the extinction at 430 nm is measured.

For fluorimetric monitoring of the enzymatic hydrolysis, excitation light with a maximum at 430 nm is chosen and the fluorescence is measured at 470 nm. At this wavelength, exclusively the fluorescence of the enzymatically split substrate is recorded.

EXAMPLE 32

To prepare the sodium salt of the sulphuric acid ester described in Example 31, 3 g of solid sodium bicarbonate are added to the mixture, after addition of 20 ml of water, and the sodium salt which crystallizes out is filtered off with suction. Purification is effected by recrystallization from water. Yellow crystals (0.7 g; 74% of theory) of melting point 254° C. (decomposition) are obtained.

The following sulphuric acid esters of the general formula

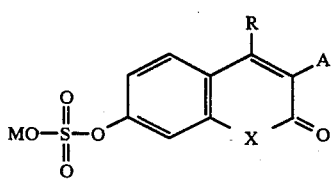

are prepared analogously using the corresponding starting compounds:

| Example | M | R | A | X | Melting point °C. |
|---------|---|---|---|---|---|
| 33 | C$_5$H$_5$NH | H | benzoxazole | O | 203–205° C. |
| 34 | C$_5$H$_5$NH | H | phenyl | O | 139° C. |
| 35 | Na | CN | benzothiazole | O | 286° C. (decomposition) |

EXAMPLE 36

1.46 g (0.83 ml; 12.5 mmol) of chlorosulphonic acid are added dropwise to 10 ml of dry pyridine, while cooling and stirring, and the pyridine-chlorosulphonic acid complex formed is then dissolved by warming. After addition of 1.1 g (2.5 mmol) of 3-(5-methyl-7-sulphobenzoxazol-2-yl)-7-hydroxy-coumarin-pyridinium salt, the mixture is warmed at 70° C. for about 5 hours. 40 ml of water are added to the solution and the pH value of the solution is brought to about 7 with 10N NaOH. The solution is evaporated to dryness with the aid of a rotary evaporator. For purification, the residue is recrystallized from ethanol/water (4:1). Yellowish crystals (1.1 g; 89% of theory) of the compound of the formula

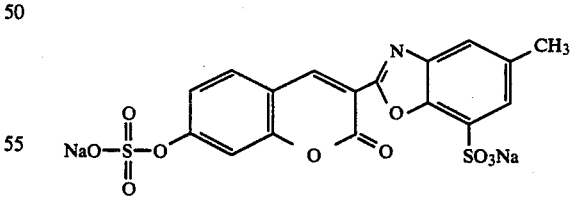

of melting point 237° C. (decomposition) are obtained.

For photometric monitoring of the enzymatic hydrolysis, the extinction at 430 nm is measured.

For monitoring the enzymatic hydrolysis by sulphatases, excitation is effected in the fluorimeter at 430 nm and the emission is measured at 470 nm. Virtually only the fluorescence of the enzymatically split substrate is recorded here.

The following sulphuric acid esters of the general formula

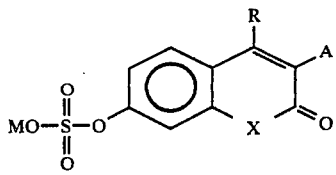

are prepared analogously using the corresponding starting compounds:

| Example | M | R | A | X |
|---|---|---|---|---|
| 37 | Na | H | 2-benzothiazolyl | O |
| 38 | K | CN | 6-methoxy-2-benzothiazolyl | O |
| 39 | Na | H | 6-ethoxy-2-benzothiazolyl | O |
| 40 | Na | CN | 2-benzoxazolyl | O |
| 41 | NH$_4$ | H | 5-chloro-2-benzoxazolyl | O |
| 42 | K | CN | 5-methyl-2-benzoxazolyl | O |
| 43 | Na | CN | 5-phenyl-1,3,4-thiadiazol-2-yl | O |
| 44 | Li | H | 5-(4-methylphenyl)-1,3,4-thiadiazol-2-yl | O |
| 45 | Na | CN | 4-oxo-3H-quinazolin-2-yl | O |
| 46 | K | CN | 1-methyl-6-methylsulfonyl-2-benzimidazolyl | O |
| 47 | Na | CN | 4-pyridyl | O |

-continued

| Example | M | R | A | X |
|---|---|---|---|---|
| 48 | NH$_4$ | H | 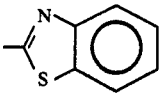 2-benzothiazolyl | N—C$_4$H$_9$—n |
| 49 | K | H | 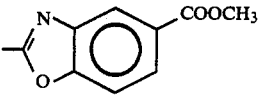 2-methyl-5-COOCH$_3$-benzoxazolyl | N—CH$_3$ |
| 50 | Na | H | 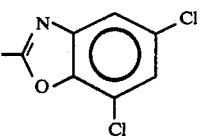 2-methyl-5,7-dichloro-benzoxazolyl | N—COOC$_2$H$_5$ |
| 51 | H$_2$N(C$_2$H$_4$OH)$_2$ | CN | 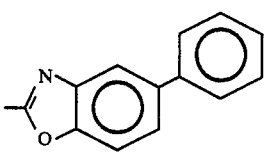 2-methyl-5-phenyl-benzoxazolyl | O |
| 52 | HN(C$_2$H$_5$)$_3$ | H | 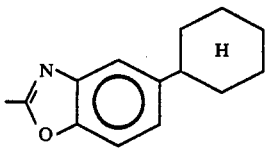 2-methyl-5-cyclohexyl-benzoxazolyl | O |
| 53 | Na | CN | 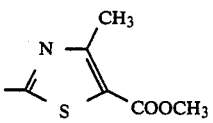 | O |
| 54 | K | CN | 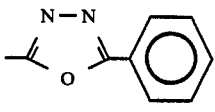 | O |
| 55 | Na | CN | CN | O |
| 56 | K | CN | COOCH$_3$ | O |
| 57 | Na | CN | SO$_2$CH$_3$ | O |
| 58 | Na | CN | SO$_2$—C$_6$H$_5$ | O |
| 59 | K | CN |  | O |

The following sulphuric acid esters, containing sulpho groups, of the general formula

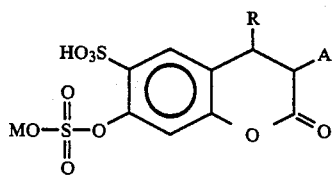

are prepared analogously using the corresponding starting compounds:

| Example | M | R | A |
|---|---|---|---|
| 60 | Na | CN | 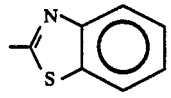 |
| 61 | K | H | 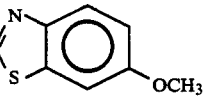 |

-continued

| Example | M | R | A |
|---|---|---|---|
| 62 | Na | CN | 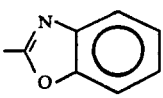 |
| 63 | Na | H | 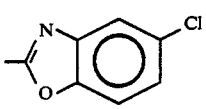 |
| 64 | Na | CN | 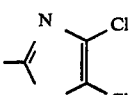 |

EXAMPLE 65

The cell in a fluorimeter is filled, at 23° C., with 3 ml of a 0.1 mmolar aqueous solution, buffered with citrate (0.05 mol of citrate/liter), of the compound from Example (1) of pH 5.2, the excitation wavelength is adjusted to 510 nm and the emission wavelength to 595 nm, 0.1 ml of the body fluid of which the acid phosphatase activity is to be determined (serum or cerebrospinal fluid) and in which the content should be of the order of size of 0.1 mg of phosphatase per ml is added and the change in the intensity of fluorescence with respect to time is monitored over a period of about 1-3 minutes in comparison with calibration curves produced beforehand. The initially linear rise in fluorescence intensity is a direct measure of the enzyme activity. In the arrangement described above, the detection limit for acid phosphatases is about $1 \times 10^{-5}$ enzyme units per ml. With known phosphatase reagents, kinetic measurement of the acid phosphatase activity with such sensitivity in this range of the spectrum has not hitherto been possible. Non-kinetic methods indeed have a similar sensitivity, but they are more tedious and expensive.

Instead of measurement of the fluorescence, the reaction can be monitored with the aid of the change in photometric light absorption at 510 nm in a completely analogous procedure, although with less sensitivity.

Acid phosphatase from potatoes (Enzyme Catalogue No. 3.1.3.2, Type IV-S), which is commercially available from Sigma Chemical Co. under No. p-1146 with an activity of 1.9 enzyme units/mg can be used as the calibration substance (the enzyme unit is defined as the amount of enzyme which hydrolyzes 1 μmol of p-nitrophenyl phoshate per minute at pH 4.8 and at 37° C.).

EXAMPLE 66

The cell in a fluorimeter is filled, at 23° C., with 3 ml of a 0.1 mmolar aqueous solution, buffered with acetate (0.05 mol of acetate/liter), of the compound from Example 31 of pH 6.2, the excitation wavelength is adjusted to 510 nm and the emission wavelength to 595 nm, 0.1 ml of the body fluid of which the sulphatase activity is to be determined (serum or cerebrospinal fluid) and in which the content should be of the order of size of 1 mg of sulphatase per ml is added and the change in the intensity of fluorescence with respect to time is monitored over a period of about 1-30 minutes in comparison with calibration curves produced beforehand. The initially linear rise in fluorescence intensity is a direct measure of the enzyme activity. In the arrangement described above, the detection limit for sulphatase is about $1 \times 10^{-3}$ enzyme units per ml. With known sulphatase reagents, kinetic measurement of the sulphatase activity with such sensitivity in this range of the spectrum has not hitherto been possible. Non-kinetic methods indeed have a similar sensitivity, but they are more tedious and expensive.

Sulphatase from Patella vulgata (Enzyme Catalogue No. 3.1.6.1, Type V), which is commercially available from Sigma Chemical Co. under No. S 8629 and has an activity of 9 enzyme units/mg can be used as the calibration substance (the enzyme unit is defined as the amount of the enzyme which hydrolyzes 1 μmol of nitrocatechol sulphate per hour at pH 5.0 and at 37° C.).

Instead of measuring the fluorescence, the reaction can be monitored by the change in photometric light absorption at 510 nm in a completely analogous procedure, although with lower sensitivity.

It will be appreciated that the instant specification and examples are set forth by way of illustration and not limitation, and that various modifications and changes may be made without departing from the spirit and scope of the present invention.

We claim:

1. A compound of the formula

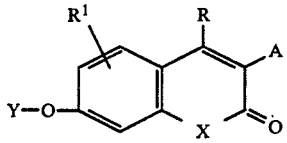

wherein

Y denotes an acid radical

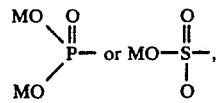

M represents hydrogen or an alkali metal, pyridinium or ammonium ion, which can be substituted by 1-4 $C_1$-$C_2$-alkyl radicals or $C_1$-$C_2$-hydroxyalkyl radicals, X represents —O— or —NQ—, Q represents hydrogen, $C_1$-$C_4$-alkyl which is optionally substituted by 1-2 OH groups, or $C_1$-$C_4$-alkoxycarbonyl, R represents hydrogen, chlorine, bromine, cyano or carbamoyl, A represents a benzoxazol-2-yl, benzothiazol-2-yl, thiazol-2-yl, benzimidazol-2-yl, quinazol-4-on-2-yl, 5-phenyl-1,3,4-thiadiazol-2-yl or 4-pyridyl radical which is optionally substituted by one or two $C_1$-$C_4$-alkyl, chlorine, $C_1$-$C_4$-alkoxy, carboxyl, $C_1$-$C_4$-alkoxycarbonyl, cyclohexyl, phenyl or sulpho radicals, and $R^1$ represents hydrogen or an $SO_3H$ group.

2. A compound according to claim 1, in which
R represents CN and
A represents a benzothiazol-2-yl or benzoxazol-2-yl radical which is optionally substituted by methyl, ethyl, chlorine, methoxy, ethoxy or sulpho.

3. A compound according to claim 1, in which
Y is

4. A compound according to claim 2, in which Y is

5. A composition for the photometric or fluorimetric determination of phosphatase or sulphatase activity in a sample comprising a carrier and an effective amount of a compound according to claim 1.

6. A composition according to claim 5, wherein the carrier is a liquid in which the active compound is dissolved.

7. A composition according to claim 5, wherein the carrier is a solid.

8. A composition for the photometric or fluorimetric determination of sulphatase activity in a sample comprising a carrier and an effective amount of a compound according to claim 3.

9. A composition according to claim 8, wherein the carrier is a liquid in which the active compound is dissolved.

10. A composition according to claim 8, wherein the carrier is solid.

11. In the photometric or fluorimetric determination of phosphatase or sulphatase activity in a sample by contacting the sample with a compound which undergoes a detectable change in dependence upon the amount of phosphatase or sulphatase activity, measuring the extent of said change, and thereby determining the amount of phosphatase or sulphatase activity in the sample, the improvement which comprises employing as the compound a compound according to claim 1.

12. In the photometric or fluorimetric determination of sulphatase activity in a sample by contacting the sample with a compound which undergoes a detectable change in the dependence upon the amount of sulphatase activity, measuring the extent of said change, and thereby determining the amount of sulphatase activity in the sample, the improvement which comprises employing as the compound a compound according to claim 3.

* * * * *